United States Patent [19]

Owens

[11] 4,209,903
[45] Jul. 1, 1980

[54] SPRINKLER HEAD TRIMMING DEVICE

[76] Inventor: Warner R. Owens, 1205 Valhalla Dr., Clearfield, Utah 84015

[21] Appl. No.: 879,159

[22] Filed: Feb. 21, 1978

[51] Int. Cl.² .......................... A01G 3/06; B26B 3/04
[52] U.S. Cl. ..................................... 30/302; 30/316; 294/50.7
[58] Field of Search ................. 294/50.7; 30/301, 302, 30/316, 300, DIG. 5, DIG. 7; 172/13, 18, 19, 22, 111, 25; 239/201, 289

[56] References Cited

U.S. PATENT DOCUMENTS

| 443,056 | 12/1890 | Potter | 172/25 X |
|---|---|---|---|
| 1,480,151 | 1/1924 | Cosman | 30/316 |
| 1,866,073 | 7/1932 | Aberle | 172/13 |
| 2,686,690 | 8/1954 | Kushnir | 294/50.7 |
| 2,882,600 | 4/1959 | Baker | 30/316 |
| 3,127,939 | 4/1964 | Rink | 30/316 |
| 3,657,814 | 4/1972 | Bohlman | 30/302 |
| 3,747,213 | 7/1973 | Green et al. | 30/300 X |

Primary Examiner—Johnny D. Cherry
Attorney, Agent, or Firm—Thorpe, North & Gold

[57] ABSTRACT

A cutting device for trimming grass and removing soil and debris from around a sprinkler head. The device includes a shaft with a handle mounted at one end to permit the user to push down and turn the device at the same time. A tubular cutting member is mounted at the other end in combination with a foot stand for enabling the user to initially push the cutting member into the ground by standing thereon. A pair of projecting blades extend from the inner surface of the tubular member and are limited in length to permit passage of the sprinkler head therebetween. These blades are also slightly pitched to develop a digging action upon rotation of the device in the ground around the sprinkler head and attached pipe. After the device is inserted into the ground and appropriately rotated, it is withdrawn with the enclosed grass, soil and debris.

11 Claims, 4 Drawing Figures

SPRINKLER HEAD TRIMMING DEVICE

BACKGROUND OF THE INVENTION

1. Field of Invention

This invention relates to landscaping tools for cutting and clearing grass from awkward locations such as sprinkler heads of permanently installed lawn sprinkling systems.

2. Prior Art

Of the various aspects of lawn care, undoubtedly one of the more frustrating duties involves trimming lawn edges and inaccessible areas around fixed objects such as sprinkler heads. Although numerous edge trimming devices have been developed, there yet remains a need for a simple device for quickly and easily clearing grass and debris from sprinkler heads which are immovably attached to a system of underground tubing for conveying water thereto.

In addition to beautification and improvement of aesthetic appearance, there are functional aspects which require removal of grass and debris from sprinkler heads. As the grass grows around the head or debris accumulates thereon, the sprinkling operation is impeded. Blockage of streamlets by overgrown grass, for example, results in uneven watering and water accumulation around the sprinkler head. It would be desirable, therefore, to have a lawn care device which is specifically adapted for trimming around sprinkler heads or similar fixed objects which project to the lawn surface.

OBJECTS AND SUMMARY OF THE INVENTION

It is an object of the present invention to provide a cutting device useful for clearing grass and debris from fixed objects such as sprinkler heads.

It is a further object of this invention to provide such a cutting device which cuts and removes soil and grass growth from the sprinkler head and coupled underground water pipe.

It is an additional object of the subject invention to provide a sprinkler trimming device which does not present a risk of damage to the sprinkler head or underground water pipe network.

These and other objects are realized in a cutting device comprising a shaft with an attached handle at one end and a tubular cutting member fixed at the other end. This device is inserted into the ground around the sprinkler head and rotated to cut and remove the enclosed grass and soil. The tubular member has a lead cutting edge which is substantially continuous in one plane to protect against puncture or other similar damage upon contact with the underground pipe. A cutting blade projects inward from the inner tube surface, making a radial cut toward the vertical pipe coupled to the sprinkler head. The length of the blade is limited such that the sprinkler head can easily pass through the tubular member without incurring any damaging contact. A slight downward pitch of the blade facilitates the retention of the tubular member in the ground during rotation thereof.

These and other objects and features of the present invention will be obvious to a person skilled in the art from the following description, taken in combination with the accompanying drawings.

DETAILED DESCRIPTION OF THE INVENTION

Referring to the Drawings

Figure 1:
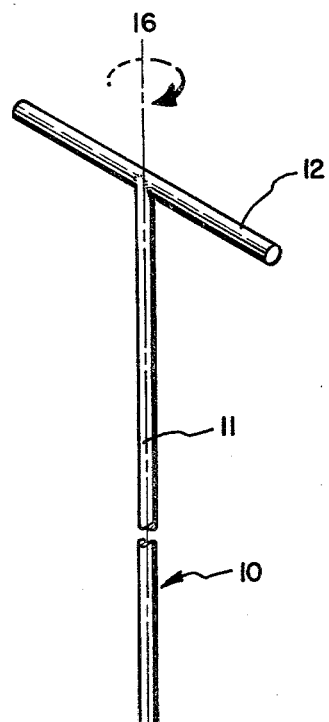
FIG. 1 is a perspective view of an embodiment of the subject invention.

A preferred embodiment of subject trimming and cutting device 10 is illustrated in FIG. 1. The device includes a supporting shaft section 11 which has a handle means 12 attached at an end thereof. The handle means 12 forms a T-section with respect to the shaft to enable a user to apply a longitudinal force at the top of the shaft. The T-section also facilitates rotation of the device, such as is explained more fully hereafter. These longitudinal and rotation forces, however, can obviously be implemented by other types of handle means which project outward from the shaft axis.

The shaft and attached handle means must be of sturdy construction to withstand torsional strain and impact stress arising with use of the device. A ⅝ inch steel bar has proven adequate for reasonable use, with a welded connection of the handle means to the end of the shaft, as shown in the figures.

The shaft 11 and handle means 12 are fixed to a tubular cutting member 13 which includes a tube body 14 having a lead cutting edge 15 which is sharpened to facilitate insertion into the ground. This tubular member is also constructed of durable material such as steel to withstand the abrasive contact with rocks and soil. The tubular member 13 is mounted in coaxial orientation with the shaft axis so that rotation of the shaft causes rotation of the tubular member about a common axis 16 therewith.

Figure 4:
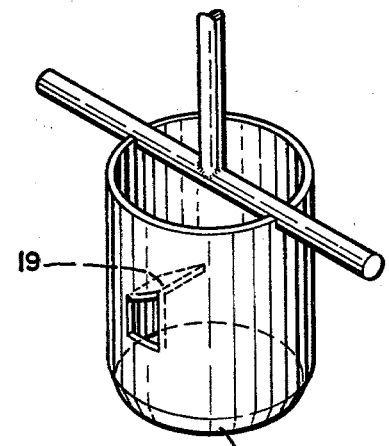
FIG. 4 illustrates a second embodiment of the present invention.

The lead cutting edge 15 is generally in a plane normal to the axis of rotation 16. With this configuration, contact of the lead edge 15 with an underground pipe section will not result in damage to the sprinkler system. Inasmuch as such pipe sections are usually constructed of a thin-walled polyvinylchloride and are not designed to withstand repeated impact from a pointed object, a puncture could result if the cutting edge were in a toothed-configuration. The most preferred embodiment for this characteristic, therefore, is illustrated in FIG. 4, wherein the lead edge 17 is continuous.

Figure 3:
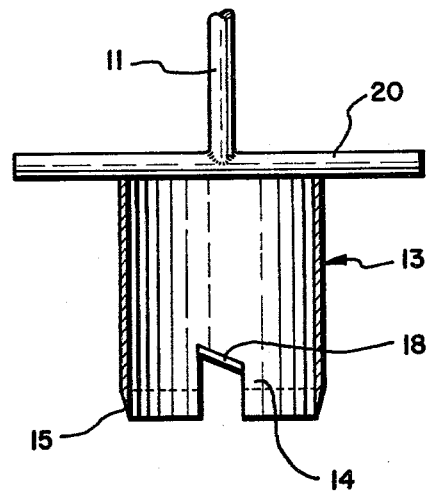
FIG. 3 is a fragmentary cross-section of the subject device, taken along line 3—3 of FIG.1.
Figure 2:
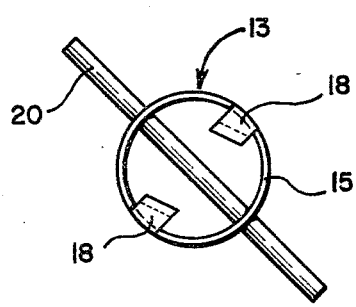
FIG. 2 is a bottom view of the device of FIG. 1.

The tubular cutting member also includes a pair of inward projecting blades 18 which are slightly pitched downward in the direction of rotation. This downward pitch causes the cutting member to dig into the ground as the device is rotated, while at the same time cutting a circumscribing radial path around the underground tube which supports the sprinkler head. Although two blades 18 are illustrated in FIGS. 1–3, a single blade 19 may be used, as shown in FIG. 4. This latter configuration is well adapted for use in places of minimal clearance, where an extending blade would not pass.

The blades are easily formed by cutting a section of tube wall along a length thereof, and bending this section toward the axis of rotation thereby forming blades having free, unobstructed ends as illustrated in the figures. It will be noted that the two cuts required to form the blade 19 are of different lengths to establish the proper pitch in relation to the lead cutting edge 17. The short length cut should precede the longer length along the direction of rotation 16 to insure that the pitch inclines downward along the rotation direction. The length of the blade should be limited so that the sprinkler head can pass through the tube hollow without being damaged by the projecting blades. This limited length also ensures adequate separation of the blade ends from the supporting pipe under the sprinkler head. It will also be apparent to one skilled in the art that a tab-like blade could be welded at the inner tube surface instead of using a bent portion of the tube wall.

This tubular cutting member can be mounted at the shaft end by numerous methods. The figures illustrate the use of a mounting bar 20 which also serves as a footstand. The mounting bar 20 which is welded to the shaft 11, is constructed of steel or similar durable material. By fixing the bar 20 in the same plane with the T-section handle means, the person using the device may stand on the mounted bar, using his weight to drive the tubular member into the ground.

The mounting bar 20 is attached to the tubular member at a pair of slots 21 and welded to secure the device in rigid configuration. The combination mounting bar 20 and top face 22 of the tube body 14 form a platform well adapted for the user to stand on.

In addition to the platform function of the mounting bar, the diametrical location of the bar serves to limit the cutting depth of the tubular member. As the bottom surface of the bar abuts against the top of the sprinkler head, further digging action by the blades is precluded. This blocking action protects underground piping from being damaged by contact with the lead cutting edge by inadvertently digging too deep. It will also be apparent that the cutting depth of the device can abe adjusted by variation of the traversing bar location within the tubular member as well as variation of blade placement.

The dimensions of the device will obviously vary in accordance with the sprinkler head dimensions. By way of illustration, a typical set of dimensions is as follows:
Shaft—⅜ in. × 32⅜ in. rod
Handle—⅜ in. × 12 in. rod
Mounting bar—⅜ in. × 16 in. rod
Tube Body—5 in. × 4¾ in.
Blade Length—½ to ⅝ in.
Blade Pitch—approx. 25°

Variation of the tube body diameter will naturally cause corresponding variation in blade length, to ensure spacial clearance with the sprinkler head and supporting pipe.

The determination of blade length should be based on the minimal cutting distance necessary to free the soil and grass from around the sprinkler and supporting pipe. If the teeth are excessive in number, size or pitch, the enclosed plug of soil can bind on the supporting pipe and wrench the sprinkler head from the system. Two blades have been found to be adequate to meet the purpose of the subject device without causing undue torsional strain to the sprinkler head and pipe.

In using the subject device, the lead cutting edge is oriented on the ground surface such that the sprinkler axis and axis of rotation for the device are in common. The user then places his weight on the footstand and drives the tubular cutting member into the ground. The blades should be positioned in the soil below ground level. The user then rotates the tubular member by turning the T-section handle. With the paired-blade configuration of FIGS. 1-3, a 180° turn is sufficient to cut a radial slice around the supporting pipe section. When the device is withdrawn from around the sprinkler, the loosened soil, grass and debris are removed, leaving the sprinkler head properly trimmed.

Where the sprinkler is adjacent a sidewalk, driveway or similar obstruction, an embodiment with a single blade (FIG. 4) can be inserted therebetween and a full rotation from one side of the sprinkler pipe to the other can be effected. Other embodiments will be apparent to those skilled in the art, and are intended to be within the scope of the invention, which invention is defined by the following claims.

I claim:

1. A cutting tool for clearing debris, grass and soil from a ground located sprinkler head while preserving a clean cut exterior grass line, comprising:
   (a) a surpporting shaft which defines an axis of rotation;
   (b) a handle means attached near one end of said shaft and projecting outward therefrom for enabling application of rotational force thereto; and
   (c) a tubular cutting member attached at the other end of said shaft in substantial coaxial orientation therewith, said tubular member having a lead cutting edge generally in a plane substantially normal to said axis for cutting a circumscribing path around the sprinkler head to obtain a properly trimmed grass line and further comprising at least one blade projecting in an inward direction only from a lower section of the inner surface of said tubular member and terminating at an unobstructed free end and having a maximum length sufficient to allow passage of said tubular member around said sprinkler head during insertion of said tubular member into the ground, said inward projecting blade having its forward cutting edge pitched at a downward slant relative to its rearward edge.

2. A cutting tool as defined in claim 1, wherein said shaft is attached at said tubular cutting member by means of a foot mount adapted to permit a user of said tool to stand thereon and thereby use his body weight to insert said tool into the ground.

3. A cutting tool as defined in claim 2, wherein said foot mount comprises a T-section extending from said supporting shaft.

4. A cutting tool as defined in claim 3, wherein said handle means comprises a T-section extending from said supporting shaft, said handle-T-section being attached to said shaft in substantial parallel orientation to said foot-T-section to facilitate the standing position thereon by the user.

5. A cutting tool as defined in claim 1, wherein said lead cutting edge is sharpened to facilitate insertion into the ground.

6. A cutting tool as defined in claim 1, further comprising a sprinkler blocking member traversing within said tubular member across a projected path for said sprinkler head, said blocking member being positioned above said lead cutting edge at a distance approximating the desired depth of cut around said sprinkler head.

7. A cutting tool as defined in claim 1, wherein said blade is formed from a section of said tubular member which is cut at two locations along the length thereof and one circumferential location towards said lead cutting edge, said section being bent inward to project into the volume contained within said tubular member and being cut to said proper terminating length.

8. A cutting tool as defined in claim 7, wherein the two cuts required to form the inward projecting blade are of different lengths, the shorter length being forward of the rearward length along its direction of rotation.

9. A cutting tool as defined in claim 1, wherein said lead cutting edge forms an uninterrupted, circular surface for preventing damage upon contact with an underground pipe coupled to said sprinkler head.

10. A cutting tool as defined in claim 1, further comprising a second inward projecting blade spaced approximately 180° from said first blade.

11. A cutting tool as defined in claim 1, wherein said blade is formed from a section of said tubular member which is cut at two locations along the length thereof and bent inward to project into the volume contained within the tubular member, the two cut locations forming respective forward and rearward edges of the inward projecting blade.

* * * * *